(12) United States Patent
Heo et al.

(10) Patent No.: US 9,788,758 B2
(45) Date of Patent: Oct. 17, 2017

(54) METHOD FOR DETERMINING ABNORMAL GAIT

(71) Applicant: Korea University Research and Business Foundation, Seoul (KR)

(72) Inventors: Hoon Heo, Seoul (KR); Hong-Youn Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 196 days.

(21) Appl. No.: 14/383,399

(22) PCT Filed: Apr. 15, 2014

(86) PCT No.: PCT/KR2014/003235
§ 371 (c)(1),
(2) Date: Sep. 5, 2014

(87) PCT Pub. No.: WO2014/171696
PCT Pub. Date: Oct. 23, 2014

(65) Prior Publication Data
US 2015/0230733 A1 Aug. 20, 2015

(30) Foreign Application Priority Data
Apr. 17, 2013 (KR) ........................ 10-2013-0042306

(51) Int. Cl.
A61B 5/103 (2006.01)
G06N 5/04 (2006.01)
A61B 5/00 (2006.01)

(52) U.S. Cl.
CPC .......... *A61B 5/1038* (2013.01); *A61B 5/6807* (2013.01); *A61B 5/7225* (2013.01);
(Continued)

(58) Field of Classification Search
CPC ... A61B 5/1038; A61B 5/6807; A61B 5/7264; A61B 5/7225; A61B 5/7278; A61B 5/7282
See application file for complete search history.

(56) References Cited

U.S. PATENT DOCUMENTS 9,179,862 B2 * 11/2015 Stergiou ............... A61B 5/1038

FOREIGN PATENT DOCUMENTS

JP 8-501958 A 3/1996
JP 2002-500768 A 1/2002
(Continued)

OTHER PUBLICATIONS

International Search Report dated Oct. 23, 2014 by the World Intellectual Property Organization in International Application No. PCT/KR2014/003235 (2 pages in English).

*Primary Examiner* — Sean Dougherty
(74) *Attorney, Agent, or Firm* — NSIP Law

(57) ABSTRACT

The invention relates to a method for determining abnormal gait comprising the following steps: (a) measuring ground reaction force generated during walking by a plurality of sensors arranged on the left-foot and the right-foot respectively; (b) applying measurements from each of the plurality of sensors to a predetermined fuzzy membership function to transform the measurements into the first fuzzy values; (c) applying the first fuzzy values to a predetermined fuzzy logic to generate the second fuzzy values for a plurality of gait phases; and (d) comparing the second fuzzy values with pre-stored data of normal gait to determine whether it is abnormal gait or not. Therefore, it is possible to determine abnormal gait more accurately even with fewer sensors.

7 Claims, 6 Drawing Sheets

(52) U.S. Cl.
CPC .......... *A61B 5/7264* (2013.01); *A61B 5/7278* (2013.01); *A61B 5/7282* (2013.01); *G06N 5/048* (2013.01)

(56) References Cited

FOREIGN PATENT DOCUMENTS

| | | |
|---|---|---|
| KR | 10-2011-0064775 A | 6/2011 |
| KR | 10-2012-0070832 A | 7/2012 |

\* cited by examiner

[Fig. 1]
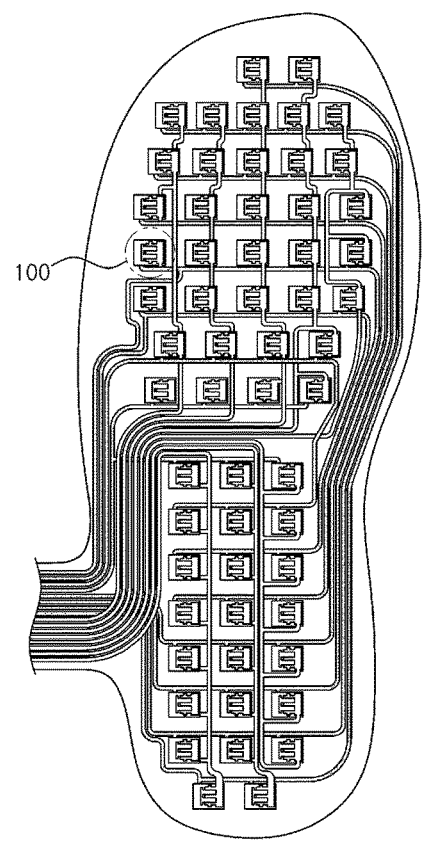

[Fig. 2]
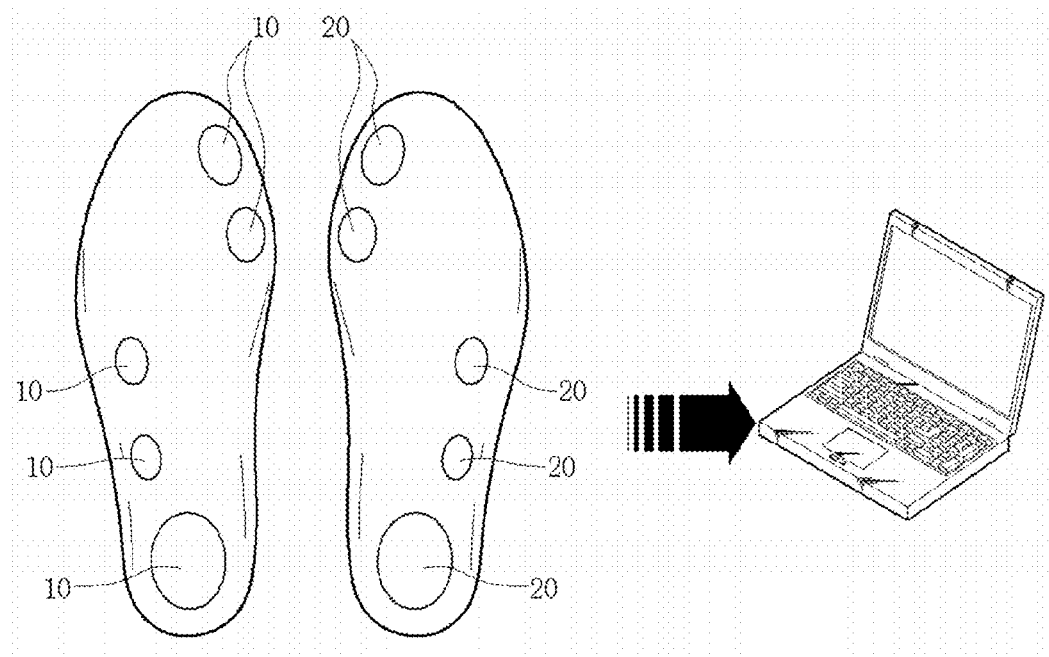

[Fig. 3]
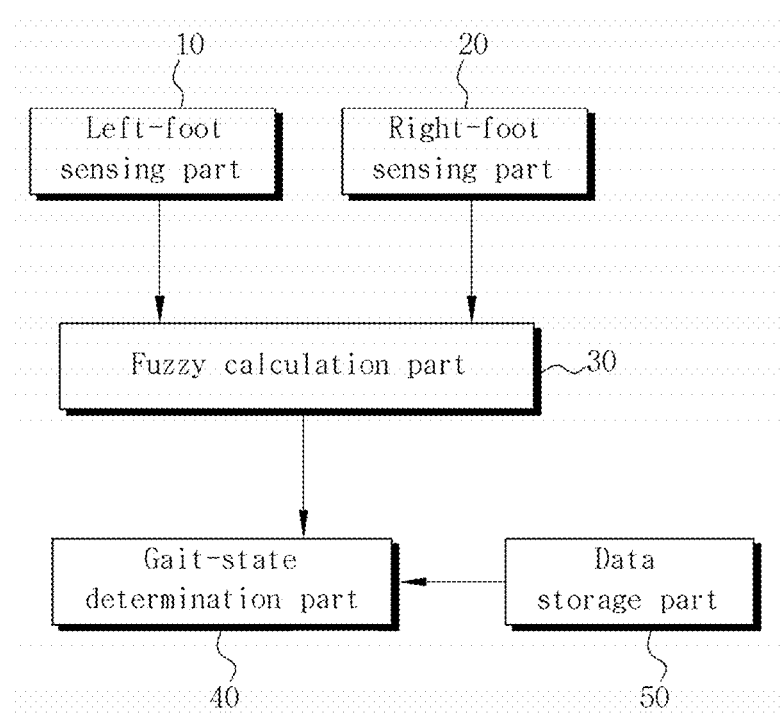

[Fig. 4]
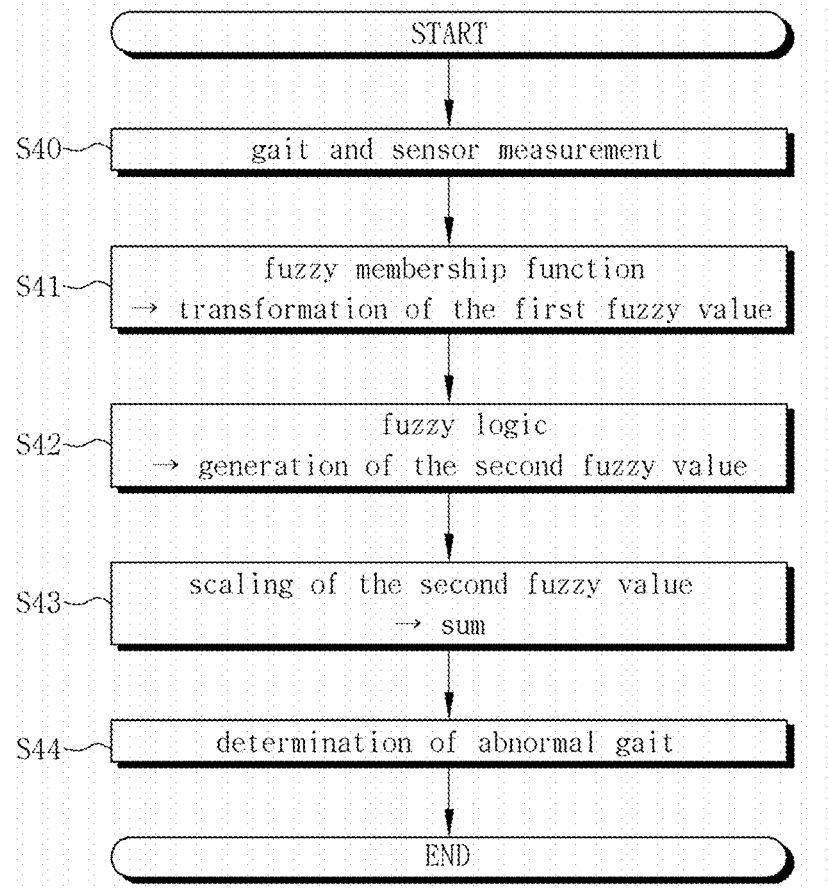

[Fig. 5]
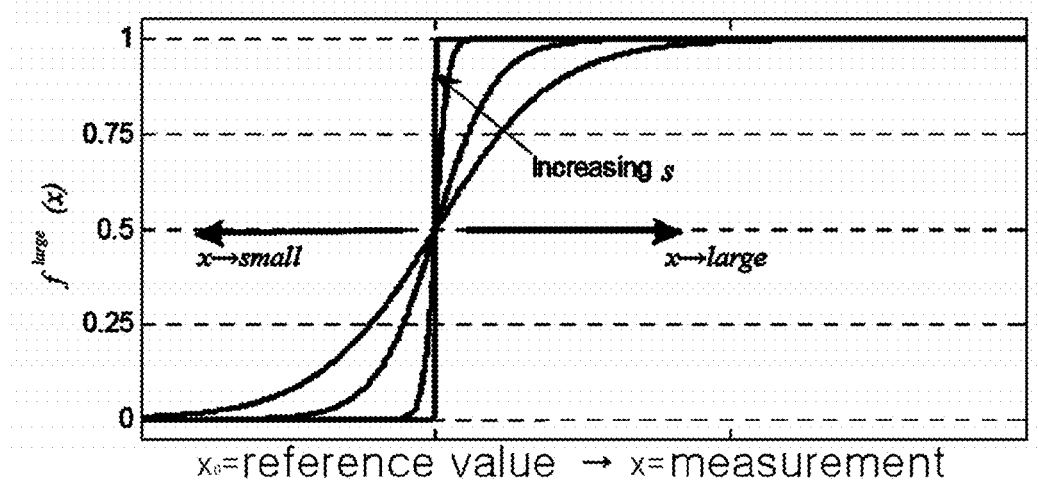

[Fig. 6]
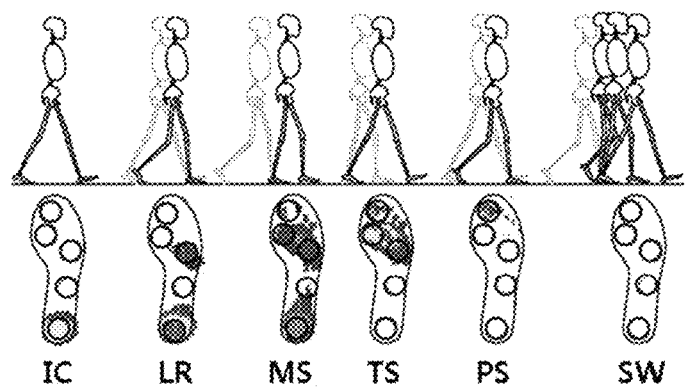

METHOD FOR DETERMINING ABNORMAL GAIT

CROSS REFERENCE TO RELATED APPLICATION(S)

This application is a National Phase entry of PCT Application No. PCT/KR2014/003235, filed on Apr. 15, 2014, which claims priority to Korean Patent Application No. 10-2013-0042306, filed on Apr. 17, 2013, the entire disclosures of each of which are incorporated herein by reference for all purposes.

TECHNICAL FIELD

The invention relates to a method for determining abnormal gait and in particular to a method for determining abnormal gait more accurately even with fewer sensors.

BACKGROUND ART

Devices for measuring and analyzing body's movement and applications therefor are needed in the field of medical treatment and sports. In one example, methods for measuring COG (Center Of Gravity) of a body and COP (Center Of Pressure) of a body are being used in the devices for measuring and analyzing body's movement.

COG and COP relate to training achievement of athletes and the measurement of the variance of COG and COP prevents falling accident and makes treatment thereof possible. Also, the measurement is used to determine gait pattern and abnormal gait.

In one example, Korean patent No. 10-0894895 titled as "Movement, Gait, and Posture Assessment and Intervention System and Method, MGPAISM" discloses that COG and COP are calculated by signals of FSR (Force Sensing Resistor) sensors for determining gait. Here, a plurality of FSR sensors are used such that the maximum FSR output is detected from measurements of the FSR sensors and it is estimated to be COP.

Also, Korean laid-open patent publication No. 10-2011-0072328 titled as "Method for Analyzing Walking Pattern" discloses that a plurality of FSR sensors are attached and 'Island' which is an error is removed from outputs of a plurality of FSR sensors.

However, in case of the Korean laid-open patent publication No. 10-2011-0072328, it is possible to make an accurate measurement by attaching many sensors onto the plantar portion, but it is costly to realize the system.

Therefore, if it is possible to determine abnormal gait accurately with fewer sensors, it would be preferable since cost for the system is reduced.

DISCLOSURE OF THE INVENTION

Technical Problem

The object of the invention is to solve the above problems and in particular, to provide a method for determining abnormal gait more accurately even with fewer sensors.

Technical Solution

To achieve the object of the invention, the invention provides a method for determining abnormal gait comprising the following steps: (a) measuring ground reaction force generated during walking by a plurality of sensors arranged on a left-foot and a right-foot of a walker respectively; (b) applying measurement values measured by each of the plurality of sensors to a predetermined fuzzy membership function to transform the measurement values into first fuzzy values; (c) applying the first fuzzy values to a predetermined fuzzy logic to generate second fuzzy values corresponding to a plurality of gait phases; and (d) comparing the second fuzzy values with pre-registered data about normal gait to determine whether the walker's gait is abnormal or not.

Here, the fuzzy membership function is defined as $$f^{Large}(x) = \frac{1}{2}\tanh(s(x - x_0)) + 1 \in [0, 1]$$

$$f^{Small}(x) = 1 - f^{Large}(x) \in [0, 1]$$

(here, $f^{Large}(x)$ and $f^{Small}(x)$ are the first fuzzy values; x is the measurement value; $x_0$ is a predetermined reference value; and s is a sensibility coefficient).

Further, in the step (c), Perry's Gait Phase is applied for the plurality of gait phases and wherein the second fuzzy values corresponding to each Perry's Gait Phase are obtained by logic operation of the first fuzzy values which are the measurement values from at least two sensors of the plurality of sensors.

Moreover, in the step (d), in the step (d), the second fuzzy values are scaled by formula $$sf(k) = \frac{1}{\sum \mu_{Phase,i(k)}}$$

(here, $\mu_{Phase,i(k)}$ is the second fuzzy value for each gait phase at time k) and the scaled values are summed up for each gait phase.

Advantageous Effect

According to the invention, it is possible to determine abnormal gait more accurately even with fewer sensors.

BRIEF DESCRIPTION OF THE DRAWINGS

FIG. 1 is a figure shown in the Korean laid-open patent publication No. 10-2011-0072328.

FIGS. 2 and 3 represent a system for determining abnormal gait to which a method for determining abnormal gait according to the present invention is applied.

FIG. 4 represents how to determine abnormal gait according to the present invention.

FIG. 5 represents small and large values, i.e., the first fuzzy values, which are determined by a fuzzy membership function according to the present invention.

FIG. 6 represents Perry's Gait Phase.

DESCRIPTION OF REFERENCE NUMERALS

10, 20: sensors
30: fuzzy calculation part
40: gait state determination part
50: data storage part

BEST MODE FOR CARRYING OUT THE INVENTION

Hereinafter, preferred embodiments according to the present invention will be explained in detail referring to attached drawings.

FIGS. 2 and 3 show systems for determining abnormal gait to which method for determining abnormal gait according to the present invention is applied. Referring to FIG. 2, the method for determining whether it is abnormal gait or not according to the present invention comprises a plurality of sensors 10 and 20 provided on the plantar portion, i.e., the sole of the foot and a measuring device for determining abnormal gait based on measurement values from sensors 10 and 20.

As shown in FIGS. 2 and 3, a plurality of sensor 10 and 20 are divided into a sensing part 10 for the left foot and a sensing part 20 for the right foot which are provided on the plantar portion of the right foot and the plantar portion of the left foot, respectively.

In one example, as shown in FIG. 2, the sensing part 10 for the left foot is provided with five sensors 10 and 20 and similarly, the sensing part 20 for the right foot is provided with five sensors 10 and 20.

The sensors 10 and 20 on the left-foot sensing part and the right-foot sensing part are configured in such a manner that two sensors are attached onto the right front of the left foot in a row and three sensors are attached onto the left back of the left foot in a row, as shown in FIG. 2, in order to measure the pressure distribution depending on the gait of the walker. Likewise, symmetrically to the left foot, the right-foot sensing part is configured such that the two sensors are attached onto the left front of the right foot in a row and three sensors are attached onto the right back of the right foot in a row. In other words, the pressure distribution of the plantar portion during walking is measured by installing only five sensors 10 and 20 on the locations where the foot of the walker is contact with the ground.

In one example of the present invention, FSR (Foot Sensor Resistor) sensor is used as means for measuring ground reaction force by sensors 10 and 20. Alternatively, air tube and air-pressure sensor can be used as a sensor to measure the pressure in the air tube, thereby determining the ground reaction force of the plantar portion.

Meanwhile, as shown in FIG. 2, a measuring device is configured in the form of data processor, e.g., computer and it comprises a fuzzy calculation part 30, a gait-state determination part 40 and a data storage part 50 as shown in FIG. 3.

The fuzzy calculation part 30 processes values measured by sensors 10 and 20 by means of a predetermined fuzzy membership function and fuzzy logic. The gait-state determination part 40 compares normal-gait data which is pre-stored in the data storage part 50 with fuzzy calculation results of the fuzzy calculation part 30 to determine whether abnormal gait.

Hereinafter, referring to FIG. 4, process for determining the gait state by the fuzzy calculation part 30 and the gait-state determination part 40 according to the present invention will be described in more detail.

When walker wears shoes having sensors 10 and 20 according to the present invention and begins walking, the ground reaction force is measured by the sensors 10 and 20 (S40) and the measurement values are transferred to the fuzzy calculation part 30.

The fuzzy calculation part 30 applies the measurement values from the sensors 10 and 20 to a predetermined fuzzy membership function and then transforms the measurement values into the first fuzzy values (S41). Here, the fuzzy membership function according to the present invention is defined by the following Formula 1.

$$f^{Large}(x) = \frac{1}{2}\tanh(s(x-x_0)) + 1 \in [0,1] \quad \text{[Formula 1]}$$
$$f^{Small}(x) = 1 - f^{Large}(x) \in [0,1]$$

$f^{Large}(x)$ and $f^{Small}(x)$ are the first fuzzy value; x is a value measured by the sensors 10 and 20; $x_0$ is a predetermined reference value; and s is a sensibility coefficient. Here, since the measurement values from the sensors 10 and 20, i.e., voltage value, vary depending on the walker's weight, etc., the sensibility coefficient is applied differently to compensate for the varying measurement values and it ranges from about 1 to 5 V.

$f^{Large}(x)$, which is fuzzy membership function, varies continuously and smoothly and is symmetrical to $f^{Small}(x)$. To determine clearly whether it is more than the reference value, the measured value is determined to be either small value or large value, which is the first fuzzy value, on the basis of the reference value $x_0$. FIG. 5 shows small value and large value, which are the fizzy value determined by the fuzzy membership function according to the present invention.

When the measurement values measured by each sensor 10 and 20 are transformed into small value or large value, the first fuzzy values are applied to the predetermined fuzzy logic to produce the second fuzzy values for a plurality of gait phases.

Here, in the method for determining the abnormal gait, Perry's Gait Phase is used as gait phases. As shown in FIG. 6, Perry's Gait Phase divides the walker's gait phases into 6 phases which comprise the following steps: 'Initial Contact (IC)', 'Loading Response (LR)', 'Mid Stance (MS)', 'Terminal Stance (TS)', 'Pre Swing (PS)', and 'Swing (SW)' sequentially.

In the present invention, fuzzy logic is set based on Perry's Gait Phase to produce the second fuzzy value for each of Perry's Gait Phase.

Here, the variation of distributed pressure is generated in each gait phase and can be expressed by the product of fuzzy membership values.

For example, when the first fuzzy value for the measurement values $x_{heel}$ of sensors 10 and 20 attached on the heel side is large and the second fuzzy value for the measurement values $x_{middle}$ of sensors 10 and 20 attached on the upper side of the heel is small, the output of the second fuzzy value will be 1. Examples of fuzzy law applied to the fuzzy logic are shown in Table 1 as follows.

TABLE 1

|  |  |  |  |  |  |
|---|---|---|---|---|---|
| Large | Small | — | — | — | $\mu_{Initial\ Contact} \rightarrow 1$ |
| Large | Large | — | Small | — | $\mu_{Loading\ Response} \rightarrow 1$ |
| Small | Large | Large | — | Small | $\mu_{Mid\ Stance} \rightarrow 1$ |
| Small | — | Large | Large | Small | $\mu_{Terminal\ Swing} \rightarrow 1$ |
| Small | — | — | Small | Large | $\mu_{Preswing} \rightarrow 1$ |
| Small | Small | Small | Small | Small | $\mu_{Swing} \rightarrow 1$ |

As shown in Table 1, the second fuzzy value is calculated by logic operation of the first fuzzy values. The first fuzzy values for the calculation of the second fuzzy value is values according to the measurement values from at least two sensors of a plurality of sensors for each Perry's Gait Phase. Here, $\mu_{Phase}$ values in Table 1 are the second fuzzy values.

Meanwhile, when the second fuzzy values are calculated as above, the sum of the second fuzzy values will be generated by scaling of the second fuzzy values (S43). The scaling and the sum are calculated by Formula 2 as follows.

$$sf(k) = \frac{1}{\sum \mu_{Phase,i(k)}} \quad \text{[Formula 2]}$$

Here, k is time and $\mu_{Phase,i(k)}$ is the second fuzzy value for each gait phase at time k. For example, $\mu_{Phase,1(k)}$ is $\mu_{Initial\ Contact}$ value at time k in Table 1 and $\mu_{Phase,2(k)}$ is $\mu_{Loading\ Response}$ value at time k in Table 1. This scaling allows the sum of output values of the fuzzy logic to be fixed at 1.

As above, when the fuzzy operation by the fuzzy logic is finished, it is determined whether it is abnormal gait or not by the comparison of the output of the fuzzy operation, i.e., the sum of scaled fuzzy values with the pre-stored data of normal gait (S44).

Here, data of the normal gait uses proportion of Perry's Gait Analysis to the gait phase. Table 2 shows proportion of Perry's Gait Analysis to the gait phase.

TABLE 2

| Phase | IC | LR | MS | TS | PS | SW |
|---|---|---|---|---|---|---|
| Portion(%) | 0~2 | 7~13 | 17~23 | 17~23 | 7~13 | 35~45 |

During the gait experiment, scaled output values of fuzzy operation are summed up to calculate the proportion and the comparison of it with the proportions in Table 2 is carried out for each phase so as to determine whether it is abnormal gait or not. Calculation of the proportion is carried out by the total sampling time and each sampling time for each phase. Further, with one test, symmetry of the right-foot and the left-foot can be determined by the comparison of proportions between the right-foot and the left-foot.

Although several exemplary embodiments of the present invention have been illustrated and described, it will be appreciated that various modifications can be made without departing from the scope and spirit of the invention as disclosed in the accompanying claims. The scope of the present invention will be determined the accompanying claims and their equivalents.

INDUSTRIAL APPLICABILITY

The invention relates to a device for determining and analyzing body's movement and its applications. For example, the invention can be applied to medical treatment field as well as sports field such as sports rehabilitation.

The invention claimed is:

1. A method for determining abnormal gait comprising:
measuring, by a plurality of sensors, ground reaction force generated during walking, wherein the plurality of sensors are arranged on a left foot and a right foot of a walker;
applying, by a fuzzy calculator, measurement values measured by each of the plurality of sensors to a predetermined fuzzy membership function to transform the measurement values into first fuzzy values;
applying, by the fuzzy calculator, the first fuzzy values to a predetermined fuzzy logic to generate second fuzzy values corresponding to a plurality of gait phases; and
comparing, by a gait-state determiner, the second fuzzy values with pre-registered data about normal gait; and
diagnosing an abnormal gait or a normal gait of the walker based on the comparison of the second fuzzy values with the pre-registered data and reporting the diagnosis to a practitioner,
wherein the fuzzy membership function is defined as $$f^{Large}(x) = \frac{1}{2}\tanh(s(x - x_0)) + 1 \in [0, 1]$$

$$f^{Small}(x) = 1 - f^{Large}(x) \in [0, 1]$$

and,
wherein $f^{Large}(x)$ and $f^{Small}(x)$ are the first fuzzy values, x is a measurement value, $x_0$ is a predetermined reference value, and s is a sensibility coefficient.

2. The method according to claim 1, wherein in the applying the first fuzzy values, Perry's Gait Phase is applied for the plurality of gait phases and wherein the second fuzzy values corresponding to each Perry's Gait Phase are obtained by logic operation of the first fuzzy values which are the measurement values from at least two sensors of the plurality of sensors, by the fuzzy calculator.

3. The method according to claim 2, wherein in the comparing, the second fuzzy values are scaled by formula $$sf(k) = \frac{1}{\sum \mu_{Phase,i(k)}}$$

(where, $\mu_{Phase,i(k)}$ is the second fuzzy value for each gait phase at time k) and the scaled values are summed up for each gait phase, by a gait-state determiner.

4. The method according to claim 1, wherein the plurality of sensors are five sensors per foot.

5. The method according to claim 4, wherein the five sensors of the plurality of sensors are positioned in the plantar region of each foot.

6. The method according to claim 4, wherein the five sensors of the plurality of sensors are pressure sensors.

7. The method according to claim 4, wherein the five sensors of the plurality of sensors are foot sensor resistor.

* * * * *